United States Patent [19]

Dunbar et al.

[11] Patent Number: 4,530,786
[45] Date of Patent: Jul. 23, 1985

[54] ANTIBODY FOR THE DETECTION AND QUANTIFICATION OF ATRAZINE

[75] Inventors: Bohn D. Dunbar, Akron; Gordon D. Niswender; James M. Hudson, both of Fort Collins, all of Colo.

[73] Assignee: Colorado State University Research Foundation, Fort Collins, Colo.

[21] Appl. No.: 647,044

[22] Filed: Sep. 4, 1984

[51] Int. Cl.$^3$ .............................................. C07G 7/00
[52] U.S. Cl. ............................ 260/112 B; 260/112 R; 260/121; 424/85; 435/7; 436/532; 436/819; 436/547
[58] Field of Search ............... 260/112 B, 112 R, 121; 424/85; 435/7; 436/532, 819, 547

[56] References Cited

U.S. PATENT DOCUMENTS

| | | | |
|---|---|---|---|
| 3,557,073 | 1/1971 | Kay | 260/112 R |
| 3,619,371 | 11/1971 | Crook et al. | 260/112 R X |
| 3,674,767 | 7/1972 | Lilly et al. | 260/112 R X |
| 3,852,157 | 12/1974 | Rubenstein et al. | 435/7 X |
| 4,007,089 | 2/1977 | Smith, III | 260/112 R X |
| 4,275,160 | 6/1981 | Singh et al. | 260/112 R X |
| 4,288,553 | 9/1981 | Singh et al. | 260/112 B X |
| 4,357,311 | 11/1982 | Schutt | 436/532 |

*Primary Examiner*—Howard E. Schain
*Attorney, Agent, or Firm*—Edwin L. Spangler, Jr.

[57] ABSTRACT

This invention relates to an antibody capable of both specifically detecting and quantifying minute quantities of the herbicide, atrazine, left in biological samples, such antibody having been made by the process of first substituting a soluble straight chain amino acid at the 4 or 6 position of 2-chloro-4(isopropylamino)-6-(ethylamino)-S-atrazine so as to leave the chlorine exposed at the 2 position along with one of the amino groups, then conjugating the resulting substitution product at the site of the amino acid group to a lysine-rich protein, using the mixed anhydride method in a strongly-basic aqueous solution, then inoculating a susceptible host with the antigen to evoke an immune response, and thereafter harvesting the antibody.

3 Claims, No Drawings

ANTIBODY FOR THE DETECTION AND QUANTIFICATION OF ATRAZINE

Farming methodology has progressed rather slowly since the plow was first introduced some 7000 years ago; however, in the last 50 years there has been a great deal of change. For instance, strip farming, stubble mulch fallow and, more recently, chemical control of weeds have altered farming practices more radically than at any time in the past.

Greb, only twenty years ago, proposed that the ideal control system would include the instant and complete killing of all unwanted vegetation shortly after harvest so as to maintain the soil essentially sterile until midsummer of the following year. The contact and pre-emergence herbicides necessary to accomplish this objective would have to be both economical and legally acceptable. His concept of the ideal control system is still valid today, but weeds, weather and various soil factors make the task of implementing such precise control extremely difficult. As yet, no single chemical or combination of chemicals capable of achieving this end have been discovered.

Atrazine, a member of the triazine family of herbicides, has been used for many years and is an inexpensive, effective and, therefore, widely used chemical for controlling weeds; however, there is a problem with atrazine because of its persistence in the soil. It is imperative, therefore, that we learn to handle this and other similar chemicals that end up as residues in the soil if our modern cropping systems are to be effective.

The present invention relates to the simple, but nonetheless vexing, problem of trying to determine just how much atrazine is left as a residue in the soil following its use several months previously. Typically, a farmer might have treated his acreage with a few pounds of atrazine in the spring of one year preparatory to planting a corn crop. He has harvested his corn in the fall of the same year and it is now September of the following year. Conditions look favorable for planting winter wheat, i.e. there is adequate moisture to get the crop started and the few weeds that have started to grow such as, for example, Kochia, corn and rough pigweed have been eradicated using contact herbicides. To insure safety of this winter wheat crop, the farmer must be sure that the amount of atrazine remaining as a residue in the soil will not kill the wheat. The present techniques for making such a determination are poor. Only a single procedure is in use presently which can be considered truly practical, in that the farmer can use it himself. The other alternative is to send soil samples to a commercial laboratory for evaluation.

Specifically, bioassay is generally regarded as an acceptable technique for analysis of residual atrazine. It is possible to set up a home bioassay system which will detect the upper range of atrazine levels known to injure winter wheat; however, one must have a suitable well-lighted and ventilated space together with a number of greenhouse pots planted with, preferably, 5 to 10 oat seeds. One also needs the skill, time and discipline necessary to carry out the assay and insure the accuracy of the results. Following germination and emergence of the seeds, each pot is thinned to contain about three plants of uniform size which are subsequently uprooted, washed clean of any soil residue and weighed to a prescribed degree of accuracy. The weights are recorded and analyzed statistically to provide a linear representation of the residual atrazine still present in the soil.

There are several drawbacks to such a bioassay, not the least of which is that it takes a minimum of twenty days to conduct these tests even if everything goes well. The lower limit of sensitivity of a bioassay is approximately 0.25 lb./acre and, at least in some types of soil, lower levels are known to be harmful to a wheat crop. It stands to reason, therefore, that if the whole purpose of the assay is to determine whether or not it is safe to plant the wheat crop and yet the assay techniques are so insensitive that such a determination cannot be reliably made, then the test may be of little value.

The second alternative open to the farmer is to send the soil samples to a commercial laboratory for testing. Some of these laboratories will employ the same bioassay technique described above while others will use modifications thereof which are better suited to the scientific environment. While certain short-cuts in the procedure are possible, they often result in less accurate results which, in an assay already pushed to its sensitivity limit, becomes risky to say the least. Such methods usually involve some type of gas chromatography or high pressure liquid chromatography.

The U.S. Environmental Protection Agency recently proposed a complex series of methods for analyzing pesticide pollutants. These procedures include many industry and contractor-developed methods, and several methods developed by the EPA's own Environmental Monitoring Support Laboratory. One of these methods uses gas chromatography for purification of the sample and the residue is detected by using a thermionic bead detector in the nitrogen mode. Detection limits for atrazines range from 30 to 70 parts per trillion; however, accuracy and precision studies suggest that samples normally contain these compounds in parts per billion, i.e. levels $10^3$ to $10^5$ times higher than the detection limit. In this range, high pressure liquid chromatography coupled with ultra-violet detection is an alternative to the gas chromatography analysis which has been accepted standard for atrazine analysis. Accuracy and expense are important factors that should be considered when these techniques are used since both methods require a great deal of purification before the sample can be quantitated. Organic material must be removed and, in some cases, several solvent systems with a complex reflux apparatus are needed. The overall result realized using these techniques is a very accurate determination (sensitive to the low PPB) of the residual herbicide in the soil sample; however, the cost of the equipment, materials, and labor is considerably higher than with any bioassay. Samples sent to a laboratory wil cost between $30.00 and $100.00 each, depending on which methods are used, and it could take several weeks or more to get the results. Moreover, several samples per field must be assayed to determine overall residual herbicide levels and the cost, therefore, becomes prohibitive.

Until recently, immunological techniques have been largely confined to medical and veterinary research, however, lately there have been some noteworthy successes in the field of horticulture, especially in the area of identification and control of various plant viruses. Specifically, the so-called "microplate enzyme linked immunosorbant assay" (ELISA) has had a significant impact on both the identification and control of several harmful pathogens. It is inexpensive, reliable and quite sensitive. Prior to the advent of this technique, while certain immunological methods were tried from time to time, they proved to be of little value in agriculture perhaps because of the cost and the high degree of technical expertise needed to carry them out. This is no longer true and the field of immunology holds great promise for agriculture. Unfortunately, realizing that immunological techniques are applicable does not solve the problem of designing and creating the antigen which will evoke the desired immune response and result in the production of an antibody specific to the molecule to be assayed.

Despite the obvious difficulties associated with attempting to hypothecate chemical make-up of an antigen that would do the job, to say nothing of producing one having such a structure, an antigen has now been synthesized which has proven specific to atrazine, moreover, the resultant immunoassay system resulting from use of the antibody is capable of quantitatively detecting atrazine in the low parts-per-billion (PPB) range. The specificity of the assay is such that there is little or no detectable immune response in the presence of even closely related compounds like, for example, hydroxyatrazine or even other metabolites. Once the antigen was produced it was injected into rabbits, which were reinjected and bled at intervals until a suitable antibody was produced. The resultant assay demonstrated a high degree of recognition for atrazine when measured by radioimmunoassay using an iodinated thyrosine methyl ester of the hapten as well as by ELISA using an ovalbumin conjugate. Several precursors, metabolites and degradation products of atrazine showed little if any reactivity in the assay. Using ELISA as a check, several soil samples containing known quantities of atrazine were subjected to the assay using the antibody forming the subject matter hereof with good correspondence of results.

It is, therefore, the principal object of the present invention to provide a unique protein-conjugated hapten effective to stimulate the production of an antibody capable of specifically detecting and also quantifying atrazine contained in biological samples.

A second objective is that of providing such an antigen which is insensitive to closely-related, yet unobjectionable, derivatives.

Another object of the invention herein disclosed and claimed is to provide an immunoassay for atrazine which has a sensitivity in the low PPB range.

An additional object is the provision of a lysine-rich protein conjugated hapten capable of attaching directly to polystyrene ELISA plates for assaying atrazine.

Other objects are to provide an antibody for atrazine assays which is easy to use, sensitive, inexpensive, safe, reliable, rapid and highly specific.

Other objects will be in part apparent and in part pointed out specifically hereinafter as the detailed description of the invention proceeds.

By way of background, haptens are molecules that by themselves are too small, or for some other reason, will not elicit an immune response. These smaller or non-immunogenic molecules must, therefore, be linked to a large protein before the resulting substance can be injected into the animal that will eventually produce the antibody. Generally, molecules with a molecular weight less that 1000 daltons need to be attached to a carrier protein. Proteins with substances linked to their side-chains are referred to as "conjugated proteins". The side groups and the protein together make up the conjugated compound that will determine the antigenic response. It is essential that a functionality be present on the molecule of interest (the hapten) which will react with a protein. In addition, of course, it must assume a specificity to atrazine without responding to the presence of other analogous compounds, particularly those like hydroxyatrazine which have little, if any, herbicidal action or other undesirable effect.

The final hapten selected for conjugation was 2-chloro-4(isopropylamino)-6-(amino caproic acid)-S-atrazine. This compound includes both exposed chlorine at the 2 position and an amino group at either the 4 or 6 position for detection by the animal's immunological mechanism or a suitable antibody-producing cell line. The amino caproic acid portion of the hapten, on the other hand, replaces either the amino ethyl or the amino isopropyl portions of the atrazine and becomes the site for conjugation to protein. While the chlorine must remain exposed at the 2 position, the hapten can be conjugated at either the amino ethyl group in the 4 position or the amino isopropyl group in the 6 position leaving the other of the amino groups exposed for detection by the response mechanism, be it alive animal or cell line. Likewise, other amino acids besides amino caproic acid can be used to derivatize the ethylamine or isopropylamine portions of the atrazine molecule. More particularly, by way of example, any of the straight chain amino acids having from a minimum of four carbon atoms out to the point at which they become so insoluble as to be ineffective, say twelve or fourteen carbons, will be effective as a replacement for the amino ethyl or the amino isopropyl portions of the hapten and thus become the site for the conjugation to protein.

The method to be described sets forth in detail the procedure followed in preparing and conjugating the above-identified hapten:

Cyanuric chloride (9.22 gm, 0.05 moles) was dissolved in 100 ml of toluene with stirring. To this was added 0.06 moles of NaOH as a 30% solution (8 ml) followed by the addition of 3 gm (0.05 mole) isopropylamine as a 70% aqueous solution. The pH was maintained at 11–12 and the mixture was stirred for 1 hour at room temperature. To the stirred reaction mixture was then added 6.56 gm (0.05 moles) of amino caproic acid dissolved in a NaOH solution (2 gm in 10 ml $H_2O$). The pH was checked and adjusted to 11–12 and maintained by addition of 30% NaOH for 1 hour, then stirred overnight at room temperature. The toluene was removed at reduced pressure on a rotary evaporator. The residue was dissolved by addition of $H_2O$ (50 ml) and brought to pH 3 with HCl. The precipitated acidic material was filtered off with vacuum on a Buchner funnel and washed well with water to remove sodium chloride. The precipitate was allowed to dry on the funnel with vacuum for several hours. Crude yield=13.5 gm (90%).

Two gm of the crude compound was taken up in ethyl acetate and placed on a silica gel column (2.5×60 cm) and eluted with ethyl acetate:hexane (80:20). After a void volume of 20 ml, 50 ml fractions were collected. Fractions 1–4 were combined and taken to dryness on an evaporator at reduced pressure. The solid residue was recrystallized two times from chloroform and one time from acetone (melting point 165°–166° C.). Yield 0.90 gms (45%) of recrystallized material.

Thin-layer chromatography was performed on silica gel (GF254) and developed with ethyl acetate:hexane (80:20) and visualized by U.V. and iodine showed a single spot at $R_f$0.65. The infrared spectrum was consistent with the desired compound. Elemental analysis was performed and the compound was found to contain 47.89% C, 6.89% H, 22.97% N and 11.89% Cl (theoretical: 47.76% C, 6.68% H, 23.21% N and 11.75% Cl).

The resultant compound was then conjugated to bovine serum albumin (BSA) and ovalbumin (OA) by the mixed anhydride method; however, other commonplace lysine-rich proteins could be used in place of the BSA or OA. The degree of conjugation was estimated at 10M Hapten/M of protein. For conjugation of the hapten to protein, the mixed anhydride method was chosen because of the very slight solubility of the hapten in anything but strongly basic aqueous solutions. Other methods at a lower pH in aqueous solution tended to precipitate the material from the protein solution before conjugation could occur.

One hundred fifty mg. (0.5 mM) of the aforementioned hapten was dissolved in 7 ml of dry N,N dimethylformamide (DMF). To this was added 0.240 ml (1.0 mM) of tri-m-butylamine and the solution cooled to 5°–10° C. in a stoppered tube. To this mixture was added 0.066 ml (0.5 mM) of isobutylchloroformate and the reaction allowed to proceed at 5°–10° C. (ice bath) for 30 min and then added in a portion to a stirred, cooled solution of 1 gm (0.0165 mM) of bovine serum alumin, 3.6 ml H20, 1 ml N NaOH and 20 ml DMF with stirring continued for 30 min. Then 1.8 ml N NaOH were added and allowed to come to room temperature with stirring overnight with the pH remaining 8 throughout the reaction. The solution was dialyzed against running water for 72 hours and brought to pH 4.5 with N HCl. The resulting precipitate was allowed to stand in the cold for several hours, collected by centrifugation and washed with cold acetone. The precipitate was suspended in water and redissolved by the addition of N NaOH to pH 7.8. The material was dialyzed against running water for 8 hours and lyophilized. Yield = 900 mg. Estimated 10 haptens linked to protein. This same hapten was conjugated to ovalbumin by the same procedure.

A thyrosine methyl ester (TME) of the hapten was also prepared and radio-iodinated with $I^{125}$. The following is a description of the procedure used to prepare the TME of the hapten for radiolabeling:

To 15 mg (0.05 mM) of hapten in 0.450 ml of dry DMF was added 0.024 ml (0.01 mole) tri-n-butylamine and the solution was cooled in ice. 0.007 ml (0.05 mM) of isobutylchloroformate was added to the solution and allowed to react in an ice bath for 30 ml and then added to a cold solution of 10 mg (0.05 mM) thyrosine methyl ester HCl in 3 ml of 50% water-DMF and 0.065 ml of 1N NaOH. Stirring in ice was continued and the solution was allowed to reach room temperature overnight, then diluted with 10 ml of cold water. The cloudy solution was extracted with ethyl acetate and the organic layer separated and washed twice with dilute HCl, once with N sodium carbonate, and then with water. The dried solution was evaporated at reduced pressure. The solid residue was dissolved in ethyl acetate and purified by preparative thin layer chromatography on silica gel (GF254, 2 mm). The plate was developed with ethyl acetate:hexane (80:20) and showed one major spot ($R_f$ 0.48). This was eluted with ether and evaporated to yield 15 mg.

New Zealand white rabbits were inoculated with the BSA-conjugated hapten, boosted at predesignated intervals and bled once a week once a titer was established. Of course, any animal suitable for production of antibodies could have been used in place of the rabbits. In fact, even antibody producing cell lines would be entirely satisfactory for antibody production.

The titer was measured by radioimmunoassay (RIA) using the TME conjugate and by enzyme linked immunosorbant assay (ELISA) using the OA-conjugated hapten. Both methods showed a high degree of recognition to atrazine after about 8 weeks and 4 boosts. It was found that atrazine could be attached directly to the polystyrene ELISA plates eliminating the need for the OA-conjugated hapten. Several precursors, metabolites and degradation products of atrazine were checked for cross reactivity. If any cross reactivity was found then serum was cleaned up on a CNBr activated superose 4B column using the compound that was causing background problems. Soil samples that contained known quantities of atrazine were extracted by various methods and checked by ELISA. The assay may vary with soil type, but under laboratory conditions in a Weld Silt loam it was possible to determine atrazine in the low PPB range.

Once the antigen is produced it is not only necessary to analyze for specificity but, in addition, to develop techniques to utilize this specificity in a practical manner. Several forms of assay could have been used. Radioimmunoassay can, for example, be used to measure any substance that can function as a hapten or antigen. Radioimmunoassay is a competitive binding test that uses a radioactive isotope, in this case the radio-iodinated thyrosine methyl ester. It is extremely sensitive, down to the nanogram level ($1 \times 10^{-9}$ g), but requires special licensing to use the radioactive material involved. A farm would not need the kind of precision that can be obtained by a RIA but once the methodology is developed it would be less expensive to run multiple tests than other laboratory methods that assay to the same degree of accuracy.

Enzyme linked immunosorbant assay appears to have the greatest promise in the field, or at least in the less well equipped laboratory. A minimum of equipment is required to perform the procedure and, once the techniques are perfected, they require no skilled technical personnel or special safety procedures to complete. The basis for the assay is a polystyrene well which will bind unselectively many organic substances. Various layers are placed in the well "sandwich" fashion until a color reaction indicates the amount of atrazine present. An inexpensive optical reader can then be used to measure the amount of atrazine present in the sample at a very modest expense.

What is claimed is:

1. The antibody for the immunoassay of atrazine made by the process of first derivatizing 2-chloro-4-(isopropylamino)-6-(ethylamino)-S-atrazine by substituting a soluble straight chain amino acid having at least four carbon atoms at either the 4 or the 6 position so as to leave the chlorine exposed at the 2 position and one of the amino groups exposed at the 4 or the 6 position, then conjugating the resulting derivative at the site of the amino acid substitution to a lysine-rich protein using the mixed anhydride method in a strongly-basic aqueous solution to produce the antigen, next inoculating a susceptible host with the antigen to evoke an immune response and thereafter harvesting the antibody from the host.

2. The antibody made in accordance with the process of claim 1 wherein: the amino acid contains between four and approximately fourteen carbon atoms.

3. The antibody made in accordance with the process of claim 1 wherein: the lysine-rich protein is selected from the group consisting of bovine serum albumin and ovalbumin.

* * * * *